United States Patent [19]

Burgio et al.

[11] Patent Number: 5,496,363
[45] Date of Patent: Mar. 5, 1996

[54] ELECTRODE AND ASSEMBLY

[75] Inventors: Paul A. Burgio, Grant Towmship, County of Washington; Richard J. Simonsen, Maplewood; Donald P. Fogle, Woodbury, all of Minn.

[73] Assignee: Minnesota Mining and Manufacturing Company, St. Paul, Minn.

[21] Appl. No.: 274,630

[22] Filed: Jul. 13, 1994

Related U.S. Application Data

[63] Continuation-in-part of Ser. No. 71,665, Jun. 2, 1993, and a continuation-in-part of Ser. No. 193,430, Feb. 8, 1994.

[51] Int. Cl.$^6$ .............................. A61N 1/04; A61B 5/04
[52] U.S. Cl. ..................... 607/152; 128/640; 128/642; 607/148
[58] Field of Search .................................. 128/639, 640, 128/642; 607/46, 47, 148, 149, 152

[56] References Cited

U.S. PATENT DOCUMENTS

| | | |
|---|---|---|
| 1,769,090 | 7/1930 | Wappler et al. . |
| 1,844,432 | 2/1932 | Lyndon . |
| 2,536,271 | 1/1951 | Fransen .................................. 128/413 |
| 3,709,228 | 1/1973 | Barker .................................... 128/410 |
| 3,720,209 | 3/1973 | Bolduc .............................. 128/2.06 E |
| 3,741,219 | 6/1973 | Sessions ................................. 128/417 |

(List continued on next page.)

FOREIGN PATENT DOCUMENTS

| | | | |
|---|---|---|---|
| 0259006A1 | 3/1988 | European Pat. Off. .......... | A61B 5/04 |
| 0337667A1 | 10/1989 | European Pat. Off. .......... | A61B 5/04 |
| 0367320A1 | 5/1990 | European Pat. Off. .......... | A61N 1/04 |
| 0369414A1 | 5/1990 | European Pat. Off. .......... | A61N 1/34 |
| 0383681A1 | 8/1990 | European Pat. Off. .......... | A61N 1/04 |
| 0390400A1 | 10/1990 | European Pat. Off. ...... | A61B 5/0416 |
| 9204620.7 | 7/1992 | Germany .......................... | A61N 1/04 |
| WO89/06554 | 7/1989 | WIPO .............................. | A61N 1/32 |

OTHER PUBLICATIONS

3M Health Care, Medical Specialties, Product Specification for No. 1522, Double Coated Medical Tape on Liner (Apr. 1, 1991).
3M Medical Specialties Product Reference Guide (Excerpts concerning No. 1522 Product) (1991).
3M 6868 Single Use Electrode Product Literature (1991).
Andersson et al., "On Acupuncture Analgesia* and the Mechanism of Pain", *Am. Journal of Chinese Medicine*, vol. 3, No. 4, pp. 311–334 (1975).
Black, R. R., "Use of transcutaneous electrical nerve stimulation in dentistry", *JADA*, vol. 113, pp. 649–652 (Oct. 1986).
Bonner, P., "Pain Control: Dentistry's Everyday Challenge", *Dentistry Today*, vol. 11, p. 70 (1992).
Hockman, R., "Neurotransmitter modulator (TENS) for control of dental operative pain", *JADA*, vol. 116, pp. 208–212 (Feb. 1988).

(List continued on next page.)

*Primary Examiner*—Angela D. Sykes
*Assistant Examiner*—Stephen Huang
*Attorney, Agent, or Firm*—Gary L. Griswold; Walter N. Kirn; John H. Hornickel

[57] ABSTRACT

TENS electrodes and connectors useful with such electrodes are disclosed. The electrodes include active electrodes and return electrodes having a common carrier with a field of pressure sensitive adhesive for adhering the electrode to a hand (finger or thumb) of the practitioner or to an applicator. Extraoral electrodes adhere to facial skin of mammals and provide TENS treatment for intraoral-procedures. The electrodes can be single channel or dual channel to combine active electrodes and return electrodes on one electrode. The connector can be single channel or dual channel and has a ridge for projecting through the tab portion of the electrode for more secure mechanical and electrical connection. Optionally, a dual channel electrode is used in combination with an elongated applicator having a bifurcated end in order to facilitate guiding a syringe needle toward a desired injection site. Assemblies of electrodes on alternative embodiments of release liners are also disclosed.

25 Claims, 8 Drawing Sheets

U.S. PATENT DOCUMENTS

| | | | |
|---|---|---|---|
| 3,972,329 | 8/1976 | Kaufman | 128/2.06 E |
| 3,977,392 | 8/1976 | Manley | 128/2.1 E |
| 4,067,342 | 1/1978 | Burton | 128/418 |
| 4,121,573 | 10/1978 | Crovella et al. | 128/640 |
| 4,213,463 | 7/1980 | Osenkarski | 128/639 |
| 4,303,073 | 12/1981 | Archibald | 128/301.13 |
| 4,304,235 | 12/1981 | Kaufman | 128/303.13 |
| 4,352,359 | 10/1982 | Larimore et al. | 128/640 |
| 4,381,789 | 5/1983 | Naser et al. | 128/798 |
| 4,398,545 | 8/1983 | Wilson | 128/798 |
| 4,458,696 | 7/1984 | Larimore | 128/798 |
| 4,524,087 | 6/1985 | Engel | 607/152 |
| 4,539,996 | 9/1985 | Engel | 128/640 |
| 4,554,924 | 11/1985 | Engel | 128/640 |
| 4,643,193 | 2/1979 | DeMarzo | 128/640 |
| 4,694,835 | 9/1987 | Strand | 128/640 |
| 4,768,969 | 9/1988 | Bauer et al. | 439/260 |
| 4,782,837 | 11/1988 | Hogan | 128/421 |
| 4,784,142 | 11/1988 | Liss et al. | 128/421 |
| 4,807,621 | 2/1989 | Hagen et al. | 128/303.13 |
| 4,842,558 | 6/1989 | Strand | 439/863 |
| 4,848,345 | 7/1989 | Zenkich | 128/419 D |
| 4,848,348 | 7/1989 | Craighead | 128/639 |
| 4,848,353 | 7/1989 | Engel | 128/640 |
| 4,852,571 | 8/1989 | Gadsby et al. | 128/640 |
| 4,865,039 | 9/1989 | Dunseath, Jr. | 128/640 |
| 4,873,974 | 10/1989 | Hagen et al. | 128/303.13 |
| 4,924,880 | 5/1990 | O'Neill et al. | 607/152 |
| 4,934,383 | 6/1990 | Glumac | 128/798 |
| 4,952,177 | 8/1990 | Drake et al. | 439/828 |
| 5,003,978 | 4/1991 | Dunseath, Jr. | 128/640 |
| 5,012,810 | 5/1991 | Strand et al. | 128/640 |
| 5,058,589 | 10/1991 | Ding et al. | 128/640 |
| 5,080,099 | 1/1992 | Way et al. | 128/640 |
| 5,133,356 | 7/1992 | Bryan et al. | 128/640 |
| 5,150,708 | 9/1992 | Brooks | 128/419 D |
| 5,180,379 | 1/1993 | Drake et al. | 606/32 |
| 5,195,523 | 3/1993 | Cartmell et al. | 128/640 |
| 5,215,087 | 6/1993 | Anderson et al. | 128/640 |
| 5,276,079 | 1/1994 | Dunn et al. | 128/640 |

OTHER PUBLICATIONS

Mannheimer et al., *Clinical Transcutaneous Electrical Nerve Stimulation*, F. A. Davis Co., pp. 352–366 (1984).

Quarnstrom Letter to Burgio dated Nov. 6, 1991.

Roth et al., "Effect of transcutaneous electrical nerve stimulation for controlling pain associated with orthodontic tooth movement", *Am. Journal of Orthodontics and Dentofacial Orthopedics*, vol. 90, No. 2, pp. 132–138 (Aug. 1986).

Schwolow et al., "Effect of transcutaneous nerve stimulation (TENS) on dental pain: comparison of psychophysical and neurophysiological data and application in dentisry", *Activ. Nerv. Sup.*, vol. 30, No. 2, pp. 129–130 (1988).

"3M Electrosurgical Patient Plates", 3M trade Literature #143 2008–5470–4 (1991).

5,496,363

ELECTRODE AND ASSEMBLY

This is a continuation-in-part application of Ser. No. 08/071,665, filed Jun. 2, 1993, and a continuation-in-part application of Ser. No. 08/193,430, filed Feb. 8, 1994, both applications incorporated by reference herein.

FIELD OF THE INVENTION

This invention relates to biomedical electrodes, especially those used for anesthesia, and more particularly to electrodes that are used with applicators.

BACKGROUND OF THE INVENTION

Biomedical electrodes have been used in a variety of applications for treatment of mammals, including the treatment of intraoral conditions.

The treatment of intraoral conditions typically involves pain or discomfort. Since the earliest days of anesthesia, attempts have been made to minimize pain or discomfort during medical and dental procedures, including intraoral-procedures.

For purposes of this invention, "intraoral-procedures" means health care manipulations by a health care practitioner done inside the oral cavity of a mammalian patient. Nonlimiting examples of intraoral-procedures include periodontal procedures, dental procedures, oral surgery, and orthodontia.

Typically, injections of local anesthetics are employed intraorally for temporary anesthesia. But these invasive procedures produce discomfort and cause high anxiety levels in patients. There is also a delay inherent between the injection and the onset of anesthesia.

Transcutaneous electrical nerve stimulation (TENS) has been employed as a method to reduce pain or discomfort for mammalian patients. Typically, the application of a low voltage, low current electrical signal through the skin counteracts nerve stimulation indicating pain or discomfort.

TENS biomedical electrodes are well known but have not previously been widely applied to intraoral-procedures. None of the TENS biomedical electrodes for intraoral-procedures were convenient to use because these electrodes were intended to stick to the soft intraoral tissue during the intraoral procedure, particularly while a cavity was being prepared and filled with restorative material. These electrodes frequently did not maintain adhesion to soft, moist tissue during these procedures in the crowded, irrigated, saliva-filled mouth. Further, saliva or irrigating fluids can drain current away from the tooth needing pain control. Another difficulty with these electrodes was the use of a splayed wire as the electrical conductor contacting the conductive adhesive in the electrode. This splayed wire could cause unacceptably high current densities.

U.S. Pat. No. 4,782,837 (Hogan) discloses a dental analgesia method and apparatus where one TENS electrode is applied to the hand and another TENS electrode is applied to the face.

TENS biomedical electrodes have employed a delivery path for electrical signals that emphasizes the surface area of the field of conductive adhesive being greater than the surface of the electrical conductor delivering the electrical signals to the field of conductive adhesive. U.S. Pat. Nos. 4,694,835 and 4,458,696 disclose TENS electrodes where perimeter dimensions of pad portions of electrical conductors are within perimeter dimensions of contiguous fields of conductive adhesives.

Thus, the present intraoral medical practices have not found a solution to a comfortable and quick administration of anesthesia.

SUMMARY OF THE INVENTION

The present invention solves the need for a comfortable and quick administration of anesthesia.

The present invention also solves an unexpected problem associated with the dimensions of the perimeter of a field of conductive adhesive relative to the perimeter dimensions of the electrical conductor delivering electrical signals to that field of conductive adhesive. This problem is one of current density. Since current density decreases significantly when traveling transversely even several millimeters through a field of conductive adhesive, it has been found in the present invention that it is important that the distance traveled by the current be minimized. The electrodes of the present invention minimize the distance traveled by the current to only a few millimeters or less of the thickness of the field of conductive adhesive.

In the present invention, the current density of TENS administration is substantially uniform due to the construction of the electrode such that the perimeter of the electrically conductive surface is beyond the perimeter of the field of conductive adhesive which the conductor contacts. Thus, the maximum distance through which current must travel is through the thickness of the conductive adhesive between the electrically conductive surface and mammalian skin.

The present invention provides an intraoral-procedures electrode for the transcutaneous electrical nerve stimulation across soft tissue in a mammalian oral cavity. The electrode comprises at least one TENS electrically conductive surface having a pad portion and a tab portion, and a field of conductive adhesive contacting each pad portion. The perimeter dimensions of each field of conductive adhesive are within perimeter dimensions of each corresponding pad portion contacted by the conductive adhesive.

The present invention also provides an intraoral TENS electrode that comprises at least one TENS electrically conductive surface having a tab portion and a pad portion on a backing material having a field of pressure sensitive adhesive for holding the TENS electrode to a hand of a practitioner or an applicator. Preferably, two TENS electrically conductive surfaces are joined to a common carrier to provide an active electrode pad and a return electrode pad. These active and return electrode pads are useful for controlling pain during injections of local anesthetics, whether intraorally or externally about the face or other locations of the mammalian body. These electrodes are also useful for other intraoral-procedures such as tooth removal, deep scaling, and other dental procedures, or for medical procedures such as wart removal.

The present invention can be used as a set of an intraoral-procedures TENS active electrode and an intraoral-procedures TENS return electrode, both applied extraorally to the facial skin of a mammal.

The present invention also provides a method of using TENS electrodes, comprising the steps of applying one intraoral-procedures electrode extraorally to facial skin of a mammal, and applying a second intraoral-procedures electrode to facial skin of a mammal.

The present invention also provides a combined TENS electrode, comprising an active electrode pad and a return electrode pad on a common carrier.

The present invention also provides an electrical connector for a biomedical electrode having at least one tab comprising a housing having an opening for insertion of each tab, a slide moveable within the housing to contact each tab, a ridge extending from the slide to extend through each tab at the point of contact with the tab, and a receptacle in the housing for receiving the ridge after extending through the tab.

A feature of the present invention is that perimeter dimensions of the electrically conductive surface are at least equal to and preferably greater than the perimeter dimensions of the field of conductive adhesive receiving the TENS electrical signals from the electrical conductor.

Another feature of the present invention is the maintenance of relative uniform current densities during TENS oral administration without significant areas of high and low current density.

Another feature of the present invention is the placement of a field of pressure sensitive adhesive on a backing material to permit the biomedical electrode to adhere to a hand (including finger or thumb) of the practitioner or to an applicator to place the electrode in a specific location.

An advantage of the present invention is the reduction in pain or discomfort in intraoral-procedures due to successful, non-invasive administration of TENS either intraorally or extraorally.

Another advantage of the present invention is the undelayed effect of TENS treatment compared relatively to the delay of the onset of anesthesia provided by injection. This advantage provides the patient with relatively immediate anesthesia and provides the practitioner with less interrupted time during treatment while waiting for the anesthesia to take effect after an injection. Too often currently, anesthesia is not complete for the patient before the practitioner is ready to begin the intraoral procedure.

Another advantage of the present invention is the controlled termination of anesthesia provided by TENS treatment for intraoral-procedures. Too often currently, anesthesia resulting from injection does not cease until well after the intraoral procedure is completed, leaving the patient with a partial anesthesia for some time after leaving the practitioner's office.

Another advantage of the present invention is that the current density of TENS administration is substantially uniform due to the construction of the intraoral-procedures electrode such that the perimeter of the electrically conductive surface is beyond the perimeter of the field of conductive adhesive which the conductor contacts. Thus, the maximum distance through which current must travel is through the thickness of the conductive adhesive between the electrically conductive surface and mammalian skin.

The present invention provides a transcutaneous electrical nerve stimulation assembly that comprises an elongated applicator having a shaft and a head connected to the shaft. The assembly also includes an electrode having an electrically conductive pad portion releasably connected to the head of the applicator. A lead is electrically coupled to the pad portion, and a means is provided to releasably connect the lead to the shaft such that the lead extends along at least a portion of the length of the shaft.

The present invention also provides a transcutaneous electrical nerve stimulation assembly that comprises an elongated applicator having a shaft and a head connected to the shaft, and the head includes a bifurcated end. The bifurcated end presents a first end section, a second end section and a channel located between the first end section and the second end section. The assembly also includes an electrode releasably connected to the head. The electrode includes a first pad portion extending over the first end section, a second pad portion extending over the second end section and a notch located between the first pad portion and the second pad portion. The notch is aligned with the channel.

Another aspect of the invention relates to a transcutaneous electrical nerve stimulation applicator that comprises an elongated shaft, and an elongated neck connected to the shaft and extending at an angle relative to the longitudinal axis of the shaft. The applicator also includes a head that is connected to the shaft, and the head includes a bifurcated end. Alternatively, the applicator can have a head at each end of the shaft with each head having a different angle.

Another aspect of the invention relates to the above described electrode used in association with the elongated applicator, as manufactured and arrayed on disposable release liners for convenient use.

A feature of the present invention is that the electrode is manufactured and stored on a combination of release liners that rapidly and conveniently permit easy placement of the electrode on an applicator or hand (finger or thumb).

An advantage of the present invention is that multiple exposed adhesive surfaces on the electrode are protected prior to usage in a manner that is not cumbersome to use of the electrode.

An advantage of the present invention is that the lead is retained against the shaft of the applicator by the adhesive, and normally does not interfere with other concurrent intraoral procedures. The lead also does not normally obstruct the practitioner's view of the oral cavity, thereby providing a convenience to the user. Additionally, the channel of the bifurcated end of the applicator, being aligned with the notch between pad portions of the electrode, provides a guide for assisting the practitioner in guiding the needle during an injection. The channel and the notch increase the accuracy of placement of the injection and enable the practitioner to avoid using his or her fingers to guide the needle, so that inadvertent puncture or other injury of the practitioner's hand from the needle can be avoided.

Embodiments of the invention are described with reference to the following drawings.

EMBODIMENTS OF THE INVENTION

Figure 1:
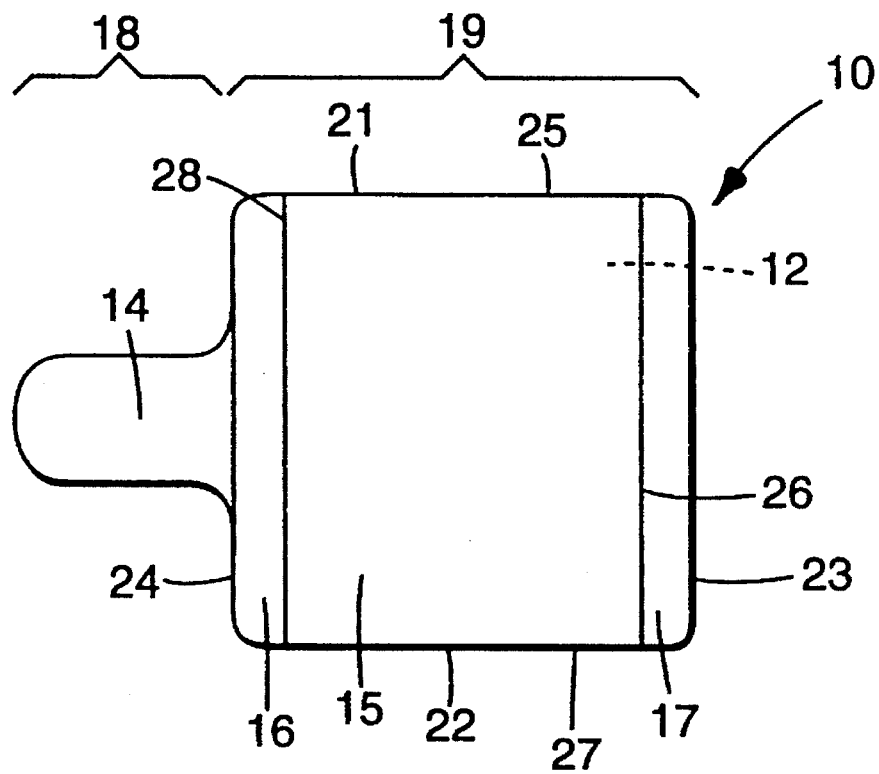
FIG. 1 is a bottom plan view of a TENS electrode according to the present invention.
Figure 2:
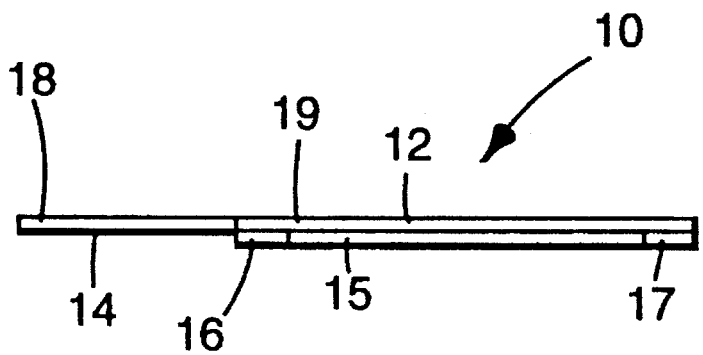
FIG. 2 is a side plan view of the TENS electrode of FIG. 1.

FIGS. 1 and 2 are bottom and side plan views, respectively, of one embodiment of an intraoral-procedures TENS electrode 10 of the present invention. From the surface farthest away from mammalian skin, electrode 10 comprises a non-conductive flexible backing 12 having an electrically conductive surface 14 contacting both a field 15 of conductive adhesive and two opposing fields 16 and 17 of biocompatible pressure sensitive skin adhesive. Not shown is a release liner that contacts fields 15, 16, and 17 of adhesive when electrode 10 is not in use. As seen in FIGS. 1 and 2, field 15 of conductive adhesive is continuous and integral, thereby contacting electrically conductive surface 14 continuously and integrally.

Flexible backing 12 comprises a tab portion 18 and a pad portion 19. Both tab portion 18 and pad portion 19 have electrically conductive surface 14, but continuous field 15 of conductive adhesive contacts only pad portion 19. Tab portion 18 is suitable for releasable attachment to a electrical connector that delivers the TENS administration.

Pad portion 19 has a perimeter defined by edges 21, 22, 23, and 24. By comparison, continuous field 15 of conductive adhesive has a perimeter defined by edges 25, 26, 27, and 28. The surface area of field 15 of conductive adhesive within edges 25-28 contacts the surface area of pad portion 19 within edges 21-24 of pad portion 19, such that the surface area of the pad portion of electrically conductive surface 14 is equal to or greater than the surface area of field 15 of conductive adhesive and such that the perimeter dimensions of the field 15 of conductive adhesive are within the perimeter dimensions of the pad portion 19 of the electrical conductive surface.

The significance of the perimeter dimensions of electrically conductive surface 14 relative to field 15 of conductive adhesive has been previously summarized in the features of the invention. A substantially uniform current density has been achieved by electrode 10 of the present invention because, while continuous field 15 of conductive adhesive is conductive, it is also more resistant to transmission of electrical signals to mammalian skin than electrically conductive surface 14. Based on the principles of Ohm's Law, the preferred delivery of TENS treatment to mammalian skin should be the path of least resistance. Constructing electrode 10 such that the maximum delivery path for TENS electrical signals is the thickness of the field 15 of conductive adhesive minimizes the resistance encountered in the delivery of TENS treatment.

Thus, a TENS electrode of the prior art with perimeter dimensions of conductive adhesive exceeding perimeter dimensions of an electrical conductor contacting that conductive adhesive provides an unwanted high current density in a narrow region of the surface area of the electrode, causing uncomfortable sensations during TENS administration. The undesirable high peak of current density could cause such pain for the mammalian patient as to itself challenge the pain of intraoral-procedures.

Fields 16 and 17 of biocompatible skin adhesive are not ionically conductive as is field 15 but are contacting pad portion 19 preferably at opposing locations to assist in the maintenance of adhesive contact of electrode 10 to skin of a mammalian patient. The opposing locations on pad portion 19 proximal and distal to tab portion 18 provide a relatively high level of adhesion to mammalian facial skin. In several mammalian species facial skin (as opposed to non-facial skin) has a high concentration of oil secreting glands that can disrupt continued adhesion of electrode 10. Since during TENS administration, mammalian patients can perceive that electrode 10 is becoming dislodged, assurance of adhesion of electrode 10 to the face throughout the intraoral procedure is important.

Unlike TENS electrodes of the prior art, use of two electrodes 10 can be adhered to a mammalian face to assist intraoral-procedures. Unexpectedly, location of electrodes 10 as an active electrode and a return electrode both extraorally on the face of a patient can provide pain relief intraorally within the jaw and mouth of the patient. While the principles are not completely understood, and not being limited to any particular theory, using two electrodes 10 can provide effective pain relief during intraoral-procedures.

Selection of materials to construct electrode 10 are known to those skilled in the art of biomedical electrode construction. U.S. Pats. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); 5,276,079 (Duan et al.); and co-pending and co-assigned U.S. patent application Ser. No. 08/101,812 (Uy et al.) all describe suitable materials for the construction of biomedical electrodes useful for TENS treatment, and all are incorporated by reference as if fully rewritten herein.

Of the numerous electrically non-conductive materials known to those skilled in the art, presently preferred for backing material 12 are polyester films of about 0.01 mm thickness commercially available as "Melinex" branded films (e.g., 329 and 339) from ICI Americas of Hopewell, Va. Preferably, the film can be treated with a corona treatment to improve the adhesion of the electrically conductive surface to the backing material.

Of the numerous electrically conductive materials known to those skilled in the art, inks containing electrical conductive particles such as graphite or metals are useful with metal-containing inks being preferred. Presently preferred for electrically conductive surface 14 is a silver loaded ink "N-30" ink or a silver/silver chloride "R-300" ink or a silver/silver chloride "R-301" ink, all commercially available from Ercon, Inc. of Waltham, Mass. Coating weights for use of the N-30 ink can be about 0.8–0.9 mg/cm$^2$ and about 0.3–0.5 mg/cm$^2$ for the R-300 and R-301 ink.

Of the numerous conductive adhesives known to those skilled in the art, presently preferred for field 15 of conductive adhesive are those conductive adhesives as described in the table at Column 16 of U.S. Pat. No. 5,012,810 (Strand et al.) and as disclosed in U.S. Pat. Nos. 4,524,087; 4,539,996; 4,848,353; and 4,554,924 (all Engel); 5,276,079 (Duan et al.); and co-pending and co-assigned U.S. Pat. application Ser. No. 08/101,812 (Uy et al.). Presently preferred for field 15 of conductive adhesive is an adhesive comprising about 26 weight percent radiation-crosslinked poly(N-vinyl pyrrolidone), about 53 weight percent glycerin, about 1.6 weight percent potassium chloride, and about 19.4 weight percent water, prepared according to U.S. Pat. No. 5,276,079 (Duan et al.) or an acrylic acid/N-vinyl-pyrrolidone copolymer plasticized with glycerol prepared according to the disclosure of U.S. Pat. No. 4,848,353 (Engel), which is incorporated by reference herein. That adhesive preferably comprises about 10 weight percent acrylic acid monomer, about 10 weight percent N-vinyl-pyrrolidone, about 51 weight percent glycerol, about 0.12 weight percent guar gum, about 3 weight percent sodium hydroxide, about 25 weight percent water, about 0.07 weight percent benzildimethylketal photoinitiator, and about 0.12 weight percent triethylene-glycol-bis-methacrylate chemical crosslinker prepared according to Example 1 of U.S. Pat. No. 4,848,353. In the event that the use of the electrode is contemplated for non-oily, non-moist skin areas, increase of water in the adhesive formulation could approach about 45 weight percent.

Of the numerous biocompatible skin adhesives known to those skilled in the art, presently preferred for fields 16 and 17 of adhesive are acrylate pressure sensitive adhesives. Acrylate ester copolymer adhesives are particularly preferred. Such materials are generally described in U.S. Pat. Nos. 2,973,286; Re 24,906; Re 33,353; 3,389,827; 4,112,213; 4,310,509; 4,323,557; 4,732,808; 4,917,928; 4,917,929; and European Patent Publication 0 051 935, all incorporated herein by reference. Presently preferred is a pressure sensitive adhesive tape commercially available as No. 1522 pressure sensitive medical tape from the Medical Specialties Department of the Consumer and Professional Health Care Division of Minnesota Mining and Manufacturing Company of St. Paul, Minn.

Figure 3:
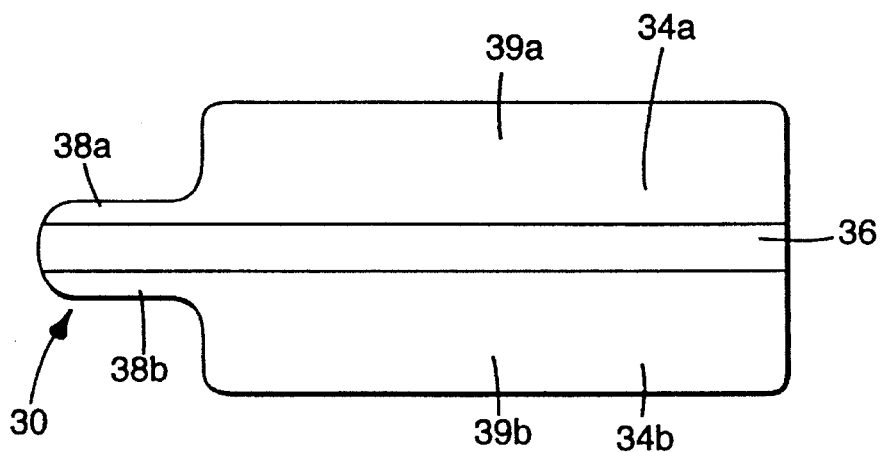
FIG. 3 is a modified bottom plan view of an alternative embodiment of the present invention having two TENS channels of stimulation.
Figure 4:
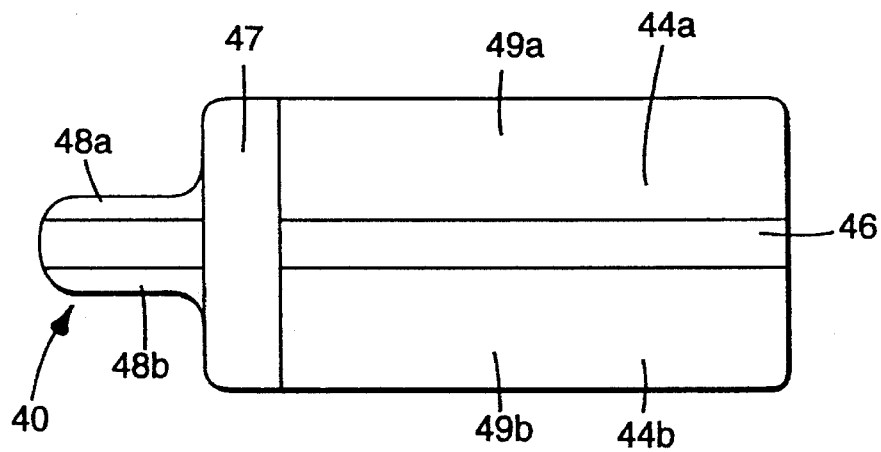
FIG. 4 is a bottom plan view of an alternative embodiment to the embodiment of FIG. 3.
Figure 5:
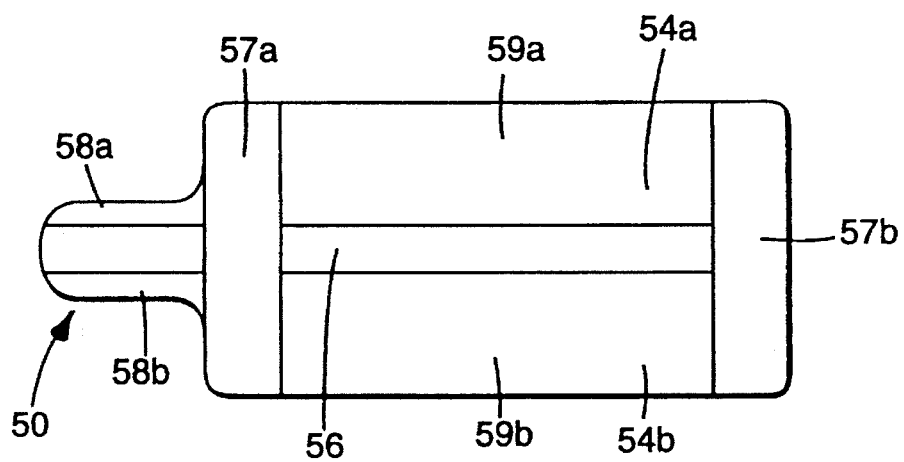
FIG. 5 is a bottom plan view of an alternative embodiment to the embodiment of FIG. 3.

Now referring to FIGS. 3–5, bottom plan views (as modified with fields of adhesive removed), three alternative embodiments of the present invention having two TENS channels of intraoral stimulation are described. Electrodes 30, 40, and 50 each differ from electrode 10 previously described in that there are two channels of TENS administration created by electrically conductive surfaces 34a, 44a, 54a, respectively, for one channel and electrically conductive surfaces 34b, 44b, and 54b, respectively, for the second channel. Thus, tab portions 38a, 48a, and 58a, respectively, and pad portions 39a, 49a, and 59a, respectively, connect to one channel, while tab portions 38b, 48b, and 58b, respectively, and pad portions 39b, 49b, and 59b connect to a second channel.

The embodiments of FIGS. 3–5 differ based on the placement of fields of biocompatible skin adhesive. In FIG. 3, a single strip 36 of biocompatible skin adhesive bisects the electrically conductive surfaces 34a and 34b. Fields of conductive adhesive (not shown) reside in contact with the surfaces 34a and 34b. In FIG. 4, strip 46 corresponds to strip 36 in FIG. 3, and electrode 40 further has a strip 47 of biocompatible skin adhesive proximal to tab portions 48a and 48b for greater assurance of adhesion during TENS treatment. FIG. 5 also shows the separation of channels between pad portions 59a and 59b using strip 56. Opposing strips 57a and 57b of biocompatible skin adhesive in FIG. 5 correspond to fields 16 and 17 of adhesive shown in FIGS. 1 and 2.

In each embodiment of FIGS. 3–5, the principle of the invention of perimeter dimensions is retained. Indeed, the total of the conductive adhesive surface areas is less than the total of the electrically conductive surfaces' areas, and the surface area of each respective field of conductive adhesive is no greater than the surface area of its respective pad portions 39a, 39b, 49a, 49b, 59a, or 59b. Further, each field of conductive adhesive has a perimeter dimension within the perimeter dimension of its respective pad portions 39a, 39b, 49a, 49b, 59a, or 59b.

Electrodes 30, 40, and 50 can be constructed from materials selected by those skilled in the art in a similar manner to those selected for electrode 10. Preferred materials for each component described for electrode 10 apply also to electrodes 30, 40, and 50.

Electrodes 30, 40, and 50 are advantageous because only one medical device is employed for two purposes. Traditionally, two devices have been required, one for each electrode purpose. Electrodes 30, 40, and 50, each having two channels of TENS administration, provide a time-savings and convenience to the health care provider while reducing cost since only one dual channel connector is required. Further, for the mammalian patient, less facial tissue is being stimulated using one dual channel electrode than if two single channel electrodes were used. With less facial tissue being stimulated, the mammalian patient generally experiences fewer tingling sensations, increasing comfort and augmenting pain control during the intraoral procedure.

Figure 6:
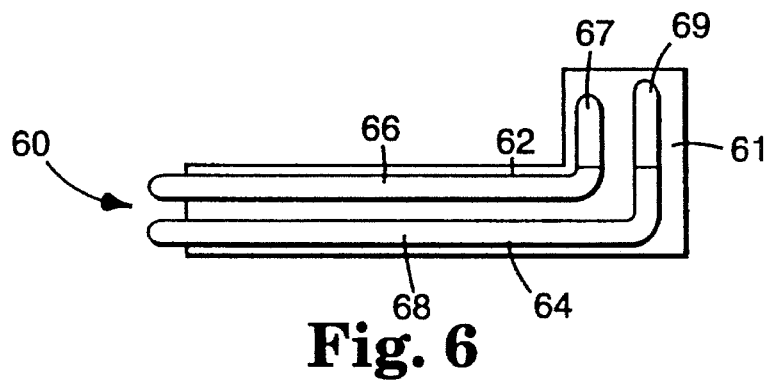
FIG. 6 is a bottom plan view of an intraoral TENS electrode of the present invention.
Figure 7:
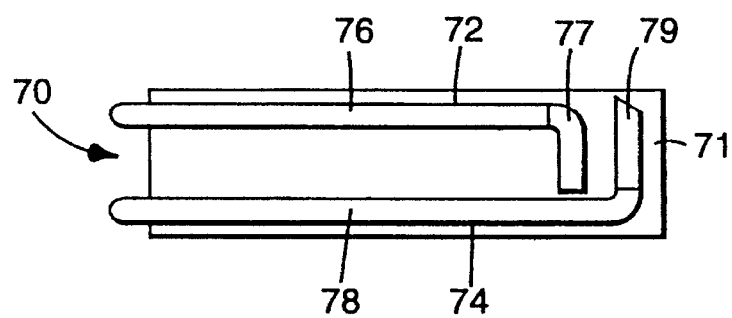
FIG. 7 is a bottom plan view of an alternative embodiment of an intraoral TENS electrode of FIG. 6.
Figure 8:
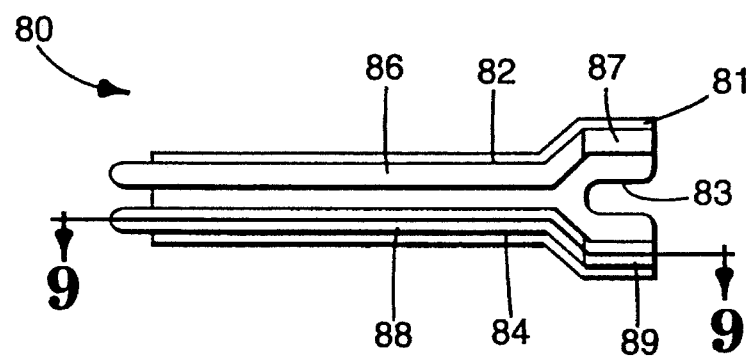
FIG. 8 is a bottom plan view of an alternative embodiment of an intraoral TENS electrode of FIG. 6.

Now referring to FIGS. 6–8, all bottom plan views, three alternative embodiments of intraoral TENS electrodes of the present invention are described. Like electrodes 30, 40, and 50, these electrodes 60, 70, and 80 each have two channels, an active channel and a return channel. Unlike electrodes 30, 40, and 50, electrodes 60, 70, and 80 are designed for intraoral TENS administration.

These embodiments of the present invention provide intraoral TENS electrodes 60, 70, and 80, each comprising at least one active electrode pad 62, 72, and 82, respectively, and at least one return electrode pad 64, 74, and 84, respectively, integrally joined to a common carrier, 61, 71, and 81, respectively. Each electrode pad 62, 64, 72, 74, 82, and 84 has a tab portion 66, 68, 76, 78, 86, and 88, respectively, and a pad portion 67, 69, 77, 79, 87, and 89, respectively, such that each tab portion has sufficient length to extend extraorally. Optionally, the common carrier is a backing material having a pressure sensitive adhesive thereon. Typically the common carrier is useful for adhesion to the gloved hand of a dental or oral practitioner for placing the TENS electrode intraorally.

Of the three embodiments, electrode 80 is preferred. Optionally, electrode 80 has a notch 83 in common carrier 81 between pads 82 and 84 to permit alignment of electrode adjacent to an injection site, preferably within notch 83.

Electrodes 60, 70, and 80 need not have both the active and return pads mounted on a common carrier. Electrodes

60, 70, and 80 can be split along the long axis to provide a separation of active and return TENS administration sites, including placement of either the active pad or the return pad intraorally and the other extraorally, or the placement of both pads intraorally in separate locations. In these embodiments, presence of the pressure sensitive adhesive on the backing material facilitates separated placement of the pads in adjustable locations for comfort and effectiveness.

Figure 9:
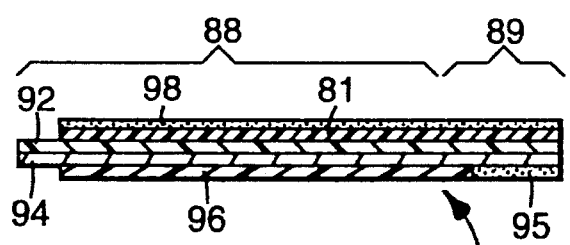
FIG. 9 is a sectional view of an alternative embodiment of the intraoral TENS electrode of FIG. 8 taken along lines 9—9.

Referring to FIG. 9, a sectional view of the embodiment of FIG. 8 along lines 9—9 is shown for pad 84, although the sectional view also demonstrates the construction of pad 82 as well as the embodiments of FIGS. 6 and 7. Pad 84 of electrode 80 has a flexible backing 92 comprising a tab portion 88 and a pad portion 89 and is adhered to common carrier 81. Both tab portion 88 and pad portion 89 have electrically conductive surfaces 94, but field 95 of conductive adhesive contacts only pad portion 89. Tab portion 88 is suitable for releasable attachment to an electrical connector that delivers the TENS. Covering field 95 at portions other than the distal end of pad 84 is a non-conductive layer 96 such as a single-coated pressure sensitive medical tape, so that field 95 only resides at the distal end of electrode pad 84. Covering common carrier 81 on the side opposing the electrically conductive surface is a field of biocompatible pressure sensitive adhesive 98 to permit pad 84 to be adhered to glove or hand of a health care practitioner, or an applicator, for intraoral placement of electrode 80. Alternatively, field 95 has sufficient adhesiveness to permit electrode 80 to adhere to less moist portions of the intraoral cavity, such as the soft palette.

Pad portion 89 has perimeter dimensions that at least exceed perimeter dimensions of field 95 in accordance with the principles of the present invention as described with respect to electrode 10 above.

Electrodes 60, 70, and 80 can be constructed from materials selected by those skilled in the art in a similar manner to those selected for electrode 10, with the addition of non-conductive layer 96 being constructed from a single-coated pressure sensitive medical tape commercially available as No. 1525L medical tape from the Medical Specialties Department of the Consumer and Professional Health Care Division of Minnesota Mining and Manufacturing Company, and the addition of field 98 being constructed from a double-coated pressure sensitive medical tape such as No. 1522 tape described above. Preferred materials for each component described for electrode 10 apply also to electrodes 60, 70, and 80.

Figure 10:
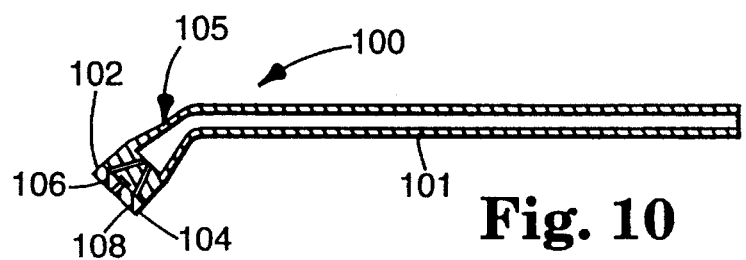
FIG. 10 is a cross-sectional view of an alternative embodiment of an intraoral TENS electrode of FIG. 6 in conjunction with an instrument to assist placement of the TENS electrode intraorally.

Referring to FIG. 10, which is a cross-sectional view of an alternative embodiment of an intraoral TENS electrode of FIG. 8 in conjunction with an instrument to assist placement of the TENS electrode intraorally. Electrode 100 is adhered to a shaft 101 providing support for both active electrode pad 102 and return electrode pad 104 with pad portions 106 and 108, respectively, extending from head 105 at the end of shaft 101. The arrangement of active electrode pad and return electrode pad to head 105 is similar to the arrangement of electrode 80. Optionally on the surface of head 105 (not shown) is a field of conductive adhesive that assists in the intraoral delivery of TENS treatment.

Selection of materials for the various components of electrode 100 can be made from materials known to those skilled in the art.

Shaft 101 can be made from autoclavable polymers such as acrylonitrile-butadiene-stryene (ABS), polycarbonate, polysulfone, polyethersulfone, or polyetherimide polymers. Presently preferred polymers are injection-molded polyetherimide or polyethersulfone polymers. Electrode pads 102 and 104 can be made from the same materials as employed for electrodes 10, 30, 40, and 50. Head 105 can be made from the same material as shaft 101. The field of pressure sensitive adhesive can be made from the same pressure sensitive adhesives as employed in electrodes 10, 30, 40, or 50. The field of conductive adhesive can be made from the same conductive adhesives as employed in electrodes 10, 30, 40, and 50.

Features of intraoral electrodes of the present invention include the following. Active and return electrode pads are parallel and in the same plane. Active and return electrode pads are attached to a common carrier, preferably in a shaft such as shaft 101 terminating at a head such as head 105. The pad portions are leads that are an integral part of the electrode pads and extend extraorally to connect to the electrical stimulation unit. The integral electrode pads and leads have an adhesive thereon that can adhere to a gloved hand or to the surface of the head of an instrument, making the electrode a disposable item while permitting reuse of the head and shaft after sterilization. The pad can deliver TENS treatment through the pad portions at the exposed surface of the head, either through a conductive adhesive or without a conductive adhesive. The active and return electrode pads are configured as shown in FIGS. 6–8 for maximum uniform pain control at the treatment site. A single electrode connector of the present invention described below can be used to connect the intraoral electrode to the TENS unit, which minimizes the number of connections and wires in and about the oral cavity during intraoral-procedures.

Figure 11:
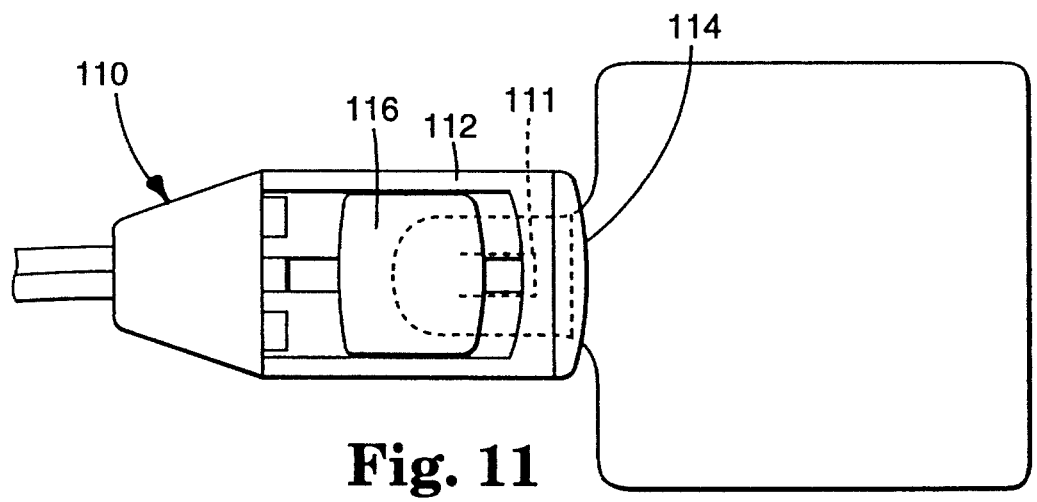
FIG. 11 is a top plan view of a connector of the present invention as used with a TENS electrode of the present invention.
Figure 12:
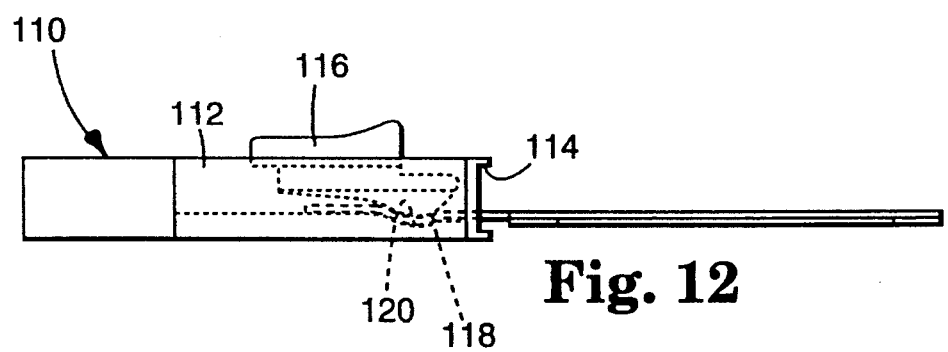
FIG. 12 is a side plan view of the connector of FIG. 11.

Now referring to FIGS. 11 and 12, top and side plan views, respectively, of a connector of the present invention for use with a TENS electrode of the present invention is described. All electrodes 10, 30, 40, 50, 60, 70, 80, and 100 require firm and unmistakable engagement with the electrical stimulation unit to maintain electrical connection for TENS treatment and continued anesthesia during intraoral-procedures. The respective tab portions of the electrodes are particularly suited for connectors that surround the tab portions and firmly and electrically contact the electrically conductive surfaces of such tab portions.

To assure mechanical connection with connector 110, the respective tab portions of the electrodes of the present invention can be modified to provide a slot opening 111, cut on two, three, or four sides, for mechanical engagement of connector 110 when electrical connection is desired.

Connector 110 improves upon a connector shown and described in U.S. Pat. No. 4,842,558 (Strand), the disclosure of which is incorporated by reference herein. Alternatively, a connector shown and described in U.S. Pat. No. 4,842,558 can be used. Connector 110 has a housing 112 having an opening 114 for insertion of each tab, a slide 116 moveable within the housing to contact a slot opening 111 in an electrode tab portion, a ridge 118 extending from the slide to extend through the slot opening 111 of the tab at the point of contact with the tab, and a receptacle 120 in the housing 112 for receiving the ridge after ridge 118 has been moved to a position where it is extending through the tab.

Slot opening 111 in the tab portion can be completely open with the cut portion (slot portion of the backing) removed or the slot portion can be cut on three sides. In the latter instance, slot opening 111 would be pushed by ridge 118 on slide 116 into the corresponding receptacle 120. In either instance, the tab portion of an electrode of the present invention would be securely held in the connector 110.

Figure 13:
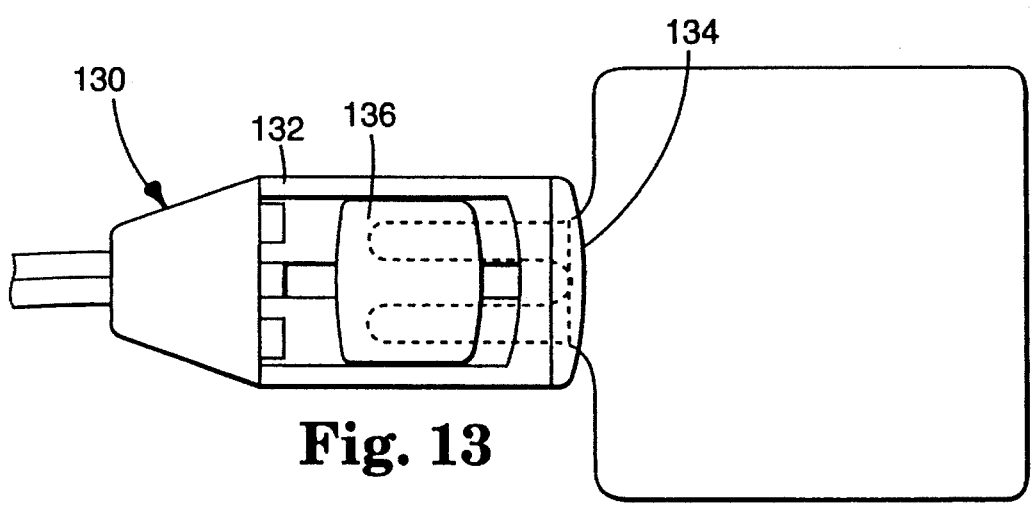
FIG. 13 is a top plan view of a connector of the present invention as used with a two channel TENS electrode of the present invention.

Electrodes 30, 40, 50, 60, 70, 80, and 100 each comprise both an active electrode channel and a return electrode channel. The proximity of the two channels on one electrode permits a single connector to be employed according to the present invention. FIG. 13 shows a top plan view of an alternate embodiment of a connector of the present invention. Connector 130 differs from connector 110, in that connector 130 has two channels corresponding to the two channels of electrodes 30, 40, 50, 60, 70, 80, and 100. Connector 130 has two electrical pathways within housing 132 such that two electrical pathways on slide 136 electrically and mechanically contact corresponding channels through opening 134 on electrode tab portions. Use of connector 130 allows one connector to attach to a single electrode yet provides the requisite two channels for TENS administration.

Alternatively, a connector 110 or 130 can have a sharp tooth replacing ridge 116 to wedge the tab of an electrode. In that instance, no slot opening is required.

Figure 14:
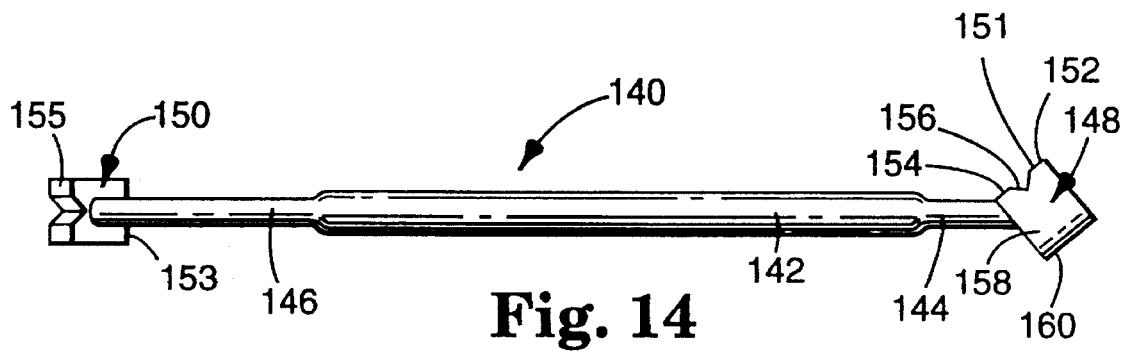
FIG. 14 is a top plan view of a TENS applicator of the present invention.
Figure 15:
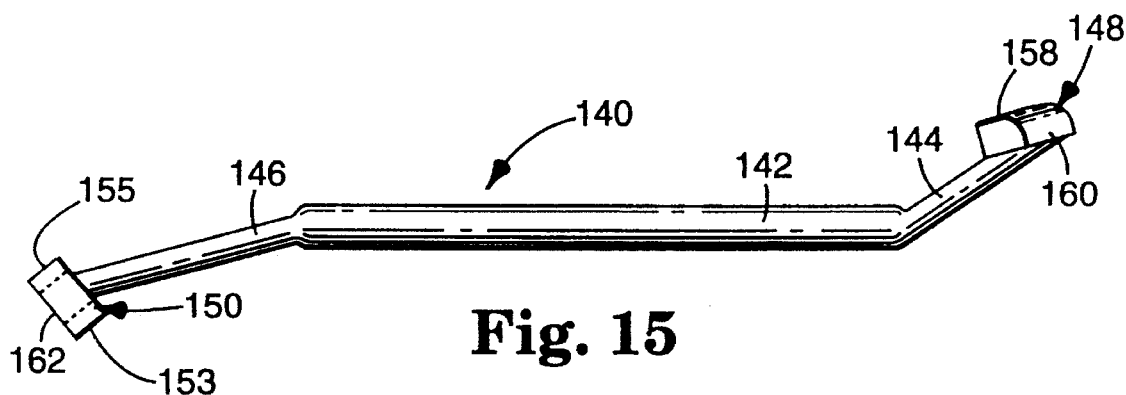
FIG. 15 is a side plan view of the applicator of FIG. 14.
Figure 16:
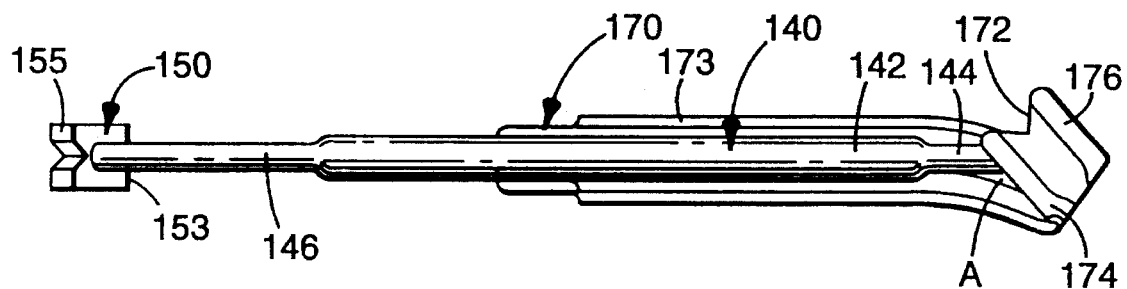
FIG. 16 is a top plan view of the applicator illustrated in FIGS. 14-15, along with a TENS electrode of the present invention.

An elongated applicator 140 as shown in FIGS. 14–16 has an elongated, cylindrical shaft 142. One end of the shaft 142 is integrally connected to a first cylindrical neck 144, while the opposite end of the shaft 142 is integrally connected to a second cylindrical neck 146. Both of the necks 144, 146 extend at an angle relative to the longitudinal axis of the shaft 142. The first neck 144 is integrally connected at its outer end to a first head 148, while the second neck 146 is integrally connected at its outer end to a second head 150.

As illustrated in FIG. 14, the first head 148 includes a bifurcated end 151 that presents a first end section 152, a second end section 154 and a generally V-shaped channel 156 located between the spaced apart end sections 152, 154. An outer wall 158 of the first head 148 extends away from the end sections 152, 154 in a flat plane, and is integrally joined to a curved wall that presents a second end 160 opposite the bifurcated end 151.

The second head 150 of the applicator 140 has a first bifurcated end 153 similar to the first bifurcated end 151 of the head 148. The first bifurcated end 153 is located on its outermost end of the second head 150 (i.e., the end of the second head 150 remote from the second neck 146). The second head 150 also has an outer wall 162 that extends in a flat plane from the first bifurcated end 153 to a second bifurcated end 155 located next to the neck 146.

The applicator 140 can be made of the same materials as mentioned earlier in connection with shaft 101 illustrated in FIG. 10. Preferably, the applicator 140 is integrally molded of a clear, translucent or opaque aromatic liquid crystal polyester such as VECTRA A530 (from Hoechst-Celanese); an alternative material is an acetal resin such as DELRIN (from E. I. dupont de Nemours & Co.). The applicator is sterilized by cold sterilization or by an autoclave or chemclave process.

FIG. 16 depicts an intraoral-procedures TENS assembly that comprises the applicator 140 along with an intraoral electrode 170. Electrode 170 is substantially the same as electrode 80 described above in connection with FIGS. 8 and 9, and as a consequence a detailed description of each element of the electrode will not be repeated.

Biocompatible pressure sensitive adhesive 173 (similar to adhesive 98), covers a common carrier and provides a means to releasably connect the electrode 170 to shaft 142 as well as to the outer wall 158 of the first head 148. Typically, the electrode 170 is spaced from the neck 144 at the location marked "A" in FIG. 16 as it extends about neck 144, to facilitate flat, firm contact of the electrode 170 with both the outer wall 158 of the first head 148 as well as with the side of the applicator shaft 142 that is remote from the first head 148. Other connecting means are also possible, such as a mechanical clip or interlocking structure.

Figure 17:
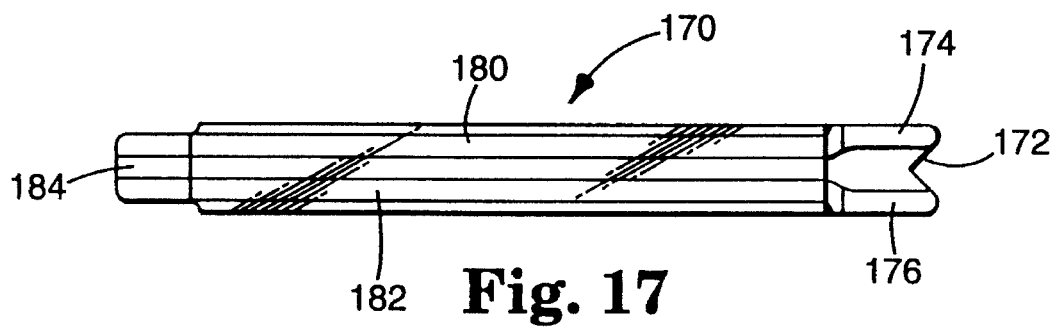
FIG. 17 is a bottom plan view of the TENS electrode alone that is shown in FIG. 16.

As shown in FIGS. 16–17, a notch 172 of the electrode 170 is located between a first pad portion 174 and a second pad portion 176. Preferably, the notch 172 is aligned with the channel 156 when the applicator 140 and the electrode 170 are assembled together. Such alignment facilitates use of the channel 156 and the notch 172 as guides to assist in alignment of the electrode 170 to a particular location in the oral cavity. For example, the needle of a syringe containing an anesthetic may be guided by the practitioner in relation to the channel 156 and the notch 172 toward an injection site in the oral cavity that is directly between the pad portions 174, 176.

Advantageously, adhesive 173 retains the electrode 170 in place against the applicator 140, such that electrode 170 does not normally obstruct the view of the practitioner toward the injection site. In this regard, the applicator 140 together with the electrode 170 can be oriented as desired in the oral cavity in such a manner as may be most useful for the situation at hand.

The electrode 170 may be connected to the applicator 140 in a variety of different configurations, and the illustration in FIG. 16 shows only one example. As an alternative, the orientation of electrode 170 may be reversed such that the notch 172 is in alignment with the channel of the first bifurcated end 153 of the second head 150. As another alternative, the pad portions 174, 176 may be placed on the second head 150 in such an orientation that the notch 172 is in alignment with the channel of the second birfucated end 155 of second head 150. The larger head 148 is useful for placement of the pad portions 174, 176 adjacent to the maxillary incisive papilla, while the smaller head 150 is useful for placing the pad portions 174, 176 in remaining areas of the patient's oral cavity.

Electrode 170 has tab portions 180, 182 (FIG. 17) that are leads and that are an integral part of the electrode portions 176, 174 respectively. FIG. 17 also illustrates a flexible backing (similar to backing 92) upon which the pad portions 174, 176, tab portions 180, 182 as well as the common carrier are mounted. A field of conductive adhesive (similar to field 95) covers the pad portions 174, 176.

Preferably, the areas of the outer walls 158, 162 are each equal to or slightly smaller than the area of the electrode 142 adjacent pad portions 174, 176. Optionally, the electrode 142 overhangs the bifurcated end of the adjacent applicator head by a distance of 2 to 4 mm, to facilitate conforming the shape of pad portions 174, 176 to the patient's tissue or skin in regions where the tissue or skin is curved.

The invention shown in FIG. 16 is especially useful for dental or medical procedures where local anesthesia is needed for only a relatively short time. Examples include injections and other intraoral procedures. Applicator 140 could be held by the practitioner, or optionally by the patient. When the assembly shown in FIG. 16 is used intraorally, tab portions 180, 182 and applicator shaft 142 are of lengths sufficient to extend extraorally when the pad portions 174, 176 are in place in the oral cavity.

Figure 18:
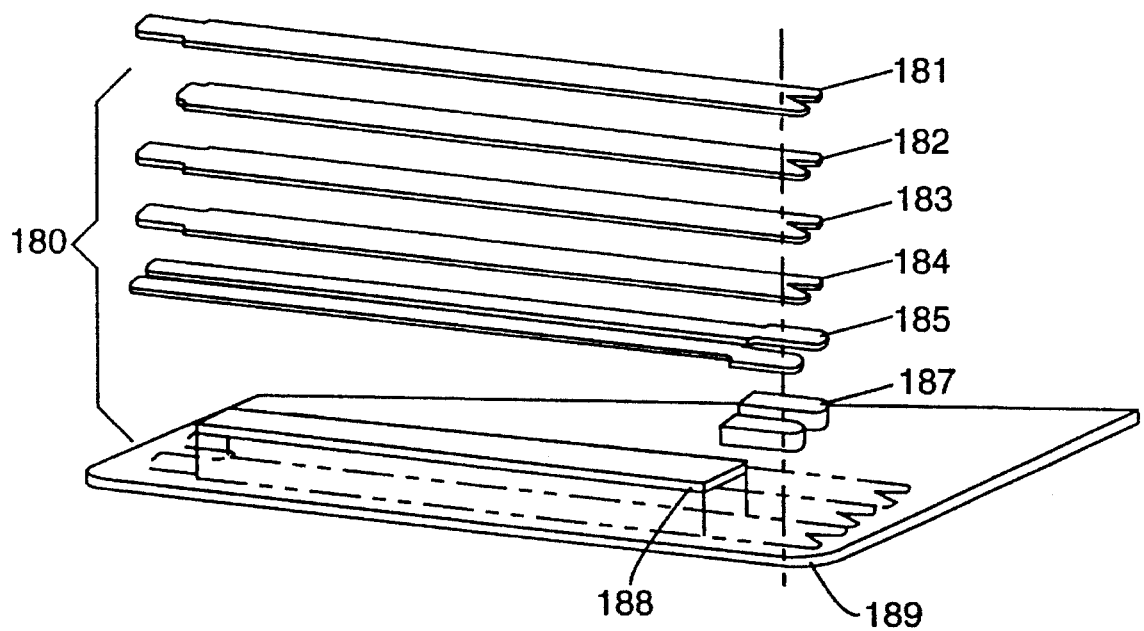
FIG. 18 is an exploded view of an electrode illustrated in FIGS. 9 and 10 as stored on release liners.
Figure 19:
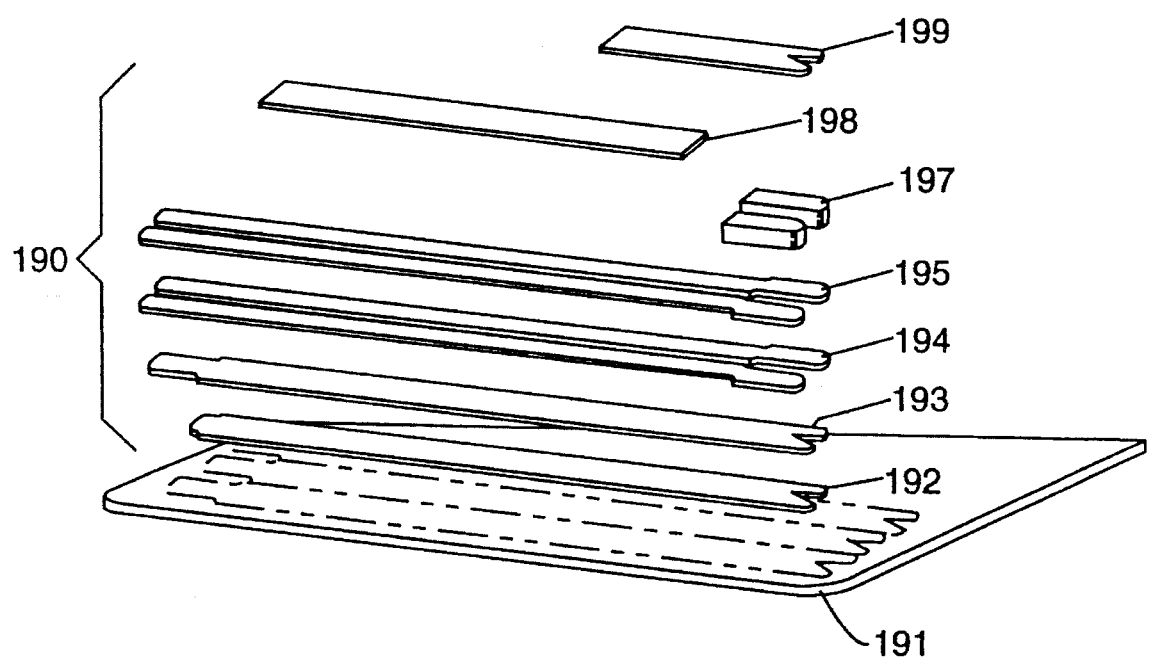
FIG. 19 is an exploded view of an electrode illustrated in FIGS. 9 and 10 as stored in an alternative embodiment of the electrode shown in FIG. 18.
Figure 20:
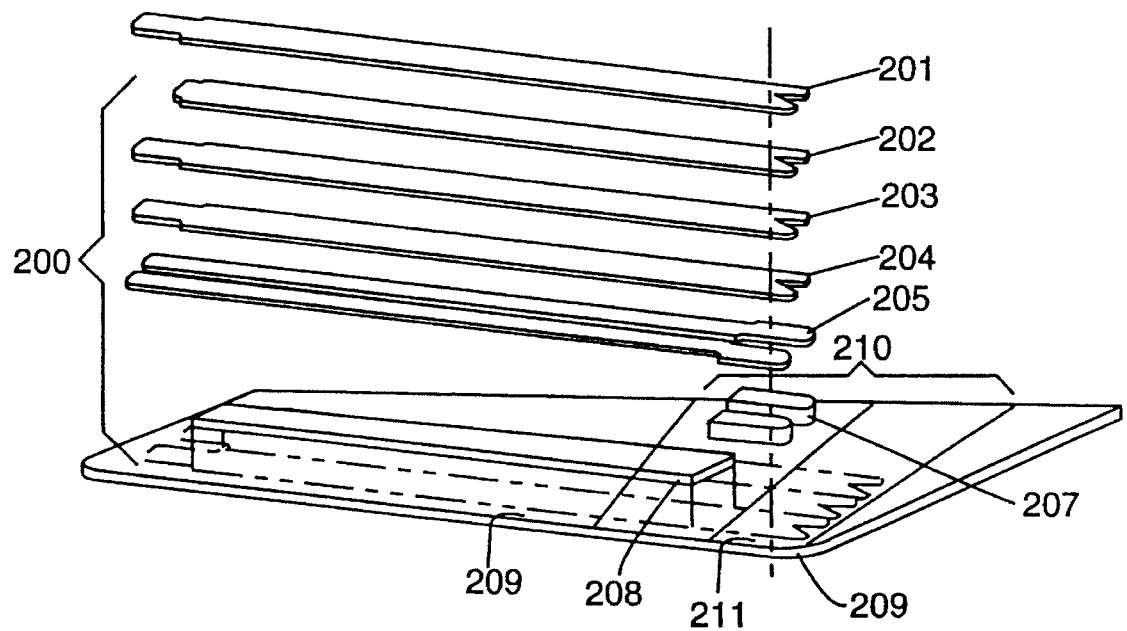
FIG. 20 is an exploded view of an electrode illustrated in FIGS. 9 and 10 as stored in a third embodiment.

Now referring to FIGS. 18–20, three embodiments of an electrode disposed on release liners are shown. Electrodes 180, 190, and 200 are the same or similar to electrode 80 and electrode 170 seen in FIGS. 9–10 and 15–17, respectively.

In the embodiment of FIG. 18, electrode 180 is protected by a siliconized high density polyethylene release liner 181 (commercially available as 4HDPE white film with No. 8000 silicone coated liner from Daubert Coated Products, Inc. of Westchester, Ill.) applied to a field 182 of pressure sensitive adhesive used for positioning on the hand or glove of a practitioner or an elongated applicator shown in FIGS. 15–17. Field 182 is in the form of double sided pressure sensitive adhesive tape commercially available from the Medical-Surgical Markets Division of Minnesota Mining and Manufacturing Company of St. Paul, Minn. as No. 1522 tape described above. Field 182 as a tape is applied to a backing strip 183 in the form of clear polyester backing commercially available from the Speciality Film Division of Minnesota Mining and Manufacturing Company as HG 90 polyethylene terephthalate film of 0.12 mm thickness. Field 182 does not need to extend the length of backing strip 183. On the opposite side of backing strip 183 is a second double sided pressure sensitive adhesive tape 184 of the same or similar construction as the tape used for field 182. This tape 184 preferably extends the entire length of backing strip 183. Applied to the adhesive surface of tape 184 is a polymeric strip 185 having on the opposing side to tape 184, a coating of metallic or graphite electrical conductor. Preferably, the strip 185 is constructed from polyester such as ICI Americas 339 film described above and utilizes Ercon ink described above extending the length of strip 185. Strip 185 extends the length of backing strip 183 to provide leads for electrical connection that extend beyond field 182 of pressure sensitive adhesive. Strip 185 preferably contains with an active and a return electrode pad according to the electrodes 80 and 170 described above in the form that permits a notch as seen in electrode 80 and electrode 170 to be employed.

Applied to pad portion of electrode 180 are fields 187 of conductive adhesive for use in contact with a patient to provide intraoral procedures TENS administration. Preferably, conductive adhesive can be any of those used for conductive adhesives for other electrodes described herein.

Adjoining fields 187 and adhering to strip 185 is a single-sided pressure sensitive adhesive tape strip 188 that shields the patient's tissue from the tab portion of the electrical conductor on strip 185. Preferably the strip 188 is a medical tape No. 1525 also commercially available from Minnesota Mining and Manufacturing Co.

Relying on the adhesiveness of the field 187 of conductive adhesive, electrode 180 is adhered to a siliconized release liner 189 commercially available from Daubert Coated Products, Inc. as No. 1642 matte finish 0.13 mm thick polyester film using the non-siliconized side.

The electrode 180 can be packaged singly or arrayed in line with one or more other electrodes 180 according to the procedures of manufacture and the preferences of storage and use. Preferably, the array of electrodes 180 on a single larger release liner 189 can be packaged to permit an easily peeled number of electrodes usable for a particular intraoral procedure.

Manufacture of electrode 180 singly or in an array of two or more can utilize rotary die cutting equipment known to those skilled in the art. Layering of the components 181–189 of electrode and release liners can be assembled sequentially or modularly.

Preferably, rotary die converting equipment conventionally used in the manufacture of biomedical electrodes that provides accurate sychronization and registry of layers can be used with layers 184, 185, and 187 assembled modularly before application of the remaining layers in sandwich format to either side thereof.

Alternatively, strip 185 can be manufactured using a gravure roll either to flood coat the ink on the polyester followed by die cutting or to print ink in the shape of the tab and pad electrically conductive surfaces. The second alternative can eliminate one roll cutting step and transfer steps.

The second alternative could also eliminate the need for tape 184 and backing strip 183.

Also, the process could be modified to eliminate strip 188 by coating the tab portion of strip 185 with an electrically insulative coating.

To use electrode 180, separation of electrode 180 from release liners 181 and 189 can be accomplished either by removing release liner 181 from electrode 180 before or after removing electrode 180 from release liner 189. Advantageously, the exposed surface of field 182 is immediately available for attachment to elongated applicator 140 or 170 described above. Alternatively, the applicator could be a self-contained electronic applicator.

FIG. 19 illustrates an alternative embodiment of electrode 180 on release liners 181 and 189. Electrode 190 is inverted on the release liners with release liner 191 corresponding to release liner 189. Release liner 199 corresponds to release liner 181, except that liner 199 only must cover the field 197 of conductive adhesive at the pad portion of the electrode 190 rather than the field 192 of adhesive that extends the length of the electrode 190. It is preferred to use tape (No. S2087 0.038 mm clear, silicone treated polyester film commercially available from H. P. Smith) or a strip of two sided coated 0.05 mm matte polyester film (with 164Z silicone release coating, the coated film being commercially available as from Daubert Coated Products) for liner 199. Other components 192–198 of electrode 190 can be made of the same materials and be of the same construction as corresponding components 182–188 of electrode 180, except that it is preferred to use a polyester tape (No. 1509 commercially available from Medical Specialities Department of Medical-Surgical Markets Division of Minnesota Mining and Manufacturing Company) for strip 198.

Similar manufacturing techniques and packaging arrays can be used for electrode 190 and release liners 191 and 199 as described above for electrode 180 and release liners 181 and 189. It is preferred to laminate components 194, 195, and 197 together as a module before layering from both opposing sides to that module. As with electrode 180, electrode 190 can be packaged singly or in an array of two or more.

An advantage of the embodiment shown in FIG. 19 is the use of a smaller area of disposable release liner 199 than release liner 181. However, removal of release liner 199 can prematurely expose the field 197 of conductive adhesive prior to removal of electrode 190 from release liner 191.

FIG. 20 shows an alternative embodiment of electrode 180 with a different configuration of release liner 189. Electrode 200 has components 202–205, 207, and 208 corresponding to components 182–185, 187 and 188 with release liner 181 corresponding to release liner 201.

Release liner 209 is different from release liner 189 in that additional adhesion is provided by a region 210 on liner 209 that is adhesive while field 207 of conductive adhesive contacts region 211 that is a release liner. Preferably region 210 is a strip of double coated tape commercially available as 3M Industrial Specialties No. 9425 High Tack/Medium tape from Minnesota Mining and Manufacturing Company and region 211 is a polymeric strip having a siliconized release surface adhered to a portion of region 210 designed to contact field 207 of conductive adhesive. Preferably, region 211 is a strip of two sided coated 0.05 mm matte polyester film (with 164Z silicone release coating, the coated film being commercially available as from Daubert Coated Products) and registered to adhere to a portion of the adhesive surface of region 210.

The embodiment shown in FIG. 20 overcomes a difficulty of employing field 207 of conductive adhesive to adhere electrode 200 to release liner 209. Region 210 can provide as much adhesion for electrode 200 as is necessary while not using the adhesiveness of field 207 for any measurable adhesion. Moreover, field 207 is less likely to delaminate from electrode 200 when electrode 200 is separated from release liner 209. Also, in use, no adhesive surface other than field 207 of conductive adhesive is provided on the surface of electrode 200 contacting the patient.

The release liner 209 of FIG. 20 can be used for any biomedical electrode when the configuration of the electrode has relatively little surface area of adhesive for holding to a release liner, especially when the surface area is a field of conductive adhesive formulated for use with mammalian skin rather than formulated for use as an adhesive for retention on a release liner.

By changing the surface properties of the release liner 209 through introduction of regions 210 and 211, one skilled in the art can configure a release liner according to the needs of the electrode during manufacture, storage, separation, and use. The advantage of release liner 209 with regions 210 and 211 is that the electrode 200 can be held releasably and securely to liner 209 prior to use but also electrode 200 can be removed with field 207 delaminating from electrode 200 and remaining in whole or in part on release liner 209 at region 211.

Various embodiments of the invention have been described. The following claims and their equivalents provide a complete understanding of the present invention.

What is claimed is:

1. An electrode for transcutaneous electrical nerve stimulation, comprising:

a TENS electrically conductive surface having a pad portion and a tab portion, wherein the electrically conductive surface has electrically conductive particles comprising metal or graphite, a field of conductive adhesive contacting the pad portion, wherein perimeter dimensions of the field of conductive adhesive are within perimeter dimensions of a corresponding pad portion of the electrically conductive surface contacted by the conductive adhesive, and at least two separate fields of biocompatible pressure sensitive adhesive contacting the pad portion at opposing locations proximal and distal to the tab portion.

2. The electrode according to claim 1, wherein surface area of the field of conductive adhesive is within surface area of the corresponding pad portion.

3. The electrode according to claim 1, wherein the field of conductive adhesive is continuous and integral.

4. The electrode according to claim 2, further comprising a common carrier including both the TENS electrically conductive surface and at least one additional TENS electrically conductive surface to provide at least two channels of TENS on the electrode.

5. A TENS electrode comprising:

a backing material having on one surface a TENS electrically conductive surface and the backing material having on a side opposing the electrically conductive surface a field of pressure sensitive adhesive for holding the TENS electrode to a hand of a practitioner or an applicator, wherein the electrode further comprises a common carrier, wherein two TENS electrically conductive surfaces are joined on the common carrier, and wherein one conductive surface comprises an active electrode pad and wherein the second conductive surface comprises a return electrode pad.

6. The electrode according to claim 5, wherein each electrically conductive surface has a tab portion and a pad portion and wherein the tab portion has sufficient length to extend extraorally when the electrode is used intraorally.

7. The electrode according to claim 5, wherein the electrode further comprises a field of conductive adhesive contacting the active electrode pad and a field of conductive adhesive contacting the return electrode pad.

8. The electrode according to claim 6, wherein the electrode further comprises a separate field of conductive adhesive contacting each pad portion of each electrically conductive surface.

9. The electrode according to claim 5, wherein the electrode further comprises a notch in the common carrier between the active electrode pad and the return electrode pad.

10. The electrode according to claim 6, wherein the electrode further comprises a notch in the common carrier between pad portions of electrically conductive surfaces.

11. A biomedical electrode assembly for storage of at least one biomedical electrode comprising:

a backing strip having on one surface an electrically conductive surface and the backing material having on the side opposing the electrically conductive surface a field of pressure sensitive adhesive for holding a biomedical electrode to a hand of a practitioner or an applicator;

a field of conductive adhesive contacting a portion of the electrically conductive surface;

a first release liner releasably covering the field of pressure sensitive adhesive; and a second release liner releasably coveting the field of conductive adhesive.

12. The assembly according to claim 11, wherein more than one biomedical electrode is included in the assembly and wherein the first release liner contacts each additional biomedical electrode.

13. The assembly according to claim 11, wherein more than one biomedical electrode is included in the assembly and wherein the second release liner contacts each additional biomedical electrode.

14. The assembly according to claim 11, wherein two electrically conductive surfaces are contained on the backing strip, and wherein one surface comprises an active electrode pad and wherein the second surface comprises a return electrode pad.

15. The assembly according to claim 14, wherein each electrically conductive surface has a tab portion and a pad portion and wherein the tab portion has sufficient length to extend extraorally when the electrode is used intraorally.

16. The assembly according to claim 14, wherein each electrically conductive surface is a TENS electrically conductive surface.

17. The assembly according to claim 14, wherein each electrically conductive surface is a metallic surface.

18. The assembly according to claim 14, wherein each electrically conductive surface is a graphite surface.

19. The assembly according to claim 11 wherein the second release liner further comprises a region of adhesiveness and a region of release surface, wherein the region of release surface contacts the field of conductive adhesive.

20. An electrode for transcutaneous electrical nerve stimulation, comprising:

a TENS electrically conductive surface having a pad portion and a tab portion, wherein the electrically conductive surface has electrically conductive particles comprising metal or graphite, and a continuous and integral field of conductive adhesive contacting the pad portion, wherein surface area of the pad portion is greater than the surface area of the continuous and integral field of conductive adhesive, and wherein perimeter dimensions of the field of conductive adhesive are within perimeter dimensions of a corresponding pad portion of the electrically conductive surface contacted by the conductive adhesive for transmission of electrical signals of a substantially uniform current density from the pad portion to mammalian skin; and wherein the electrode further comprises a common carrier including both the TENS electrically conductive surface and at least one additional TENS electrically conductive surface to provide at least two channels of TENS on the electrode.

21. The electrode according to claim 20, further comprising at least one field of biocompatible pressure sensitive adhesive contacting the pad portion.

22. The electrode according to claim 20, wherein at least two separate fields of biocompatible pressure sensitive adhesive contact the pad portion at opposing locations proximal and distal to the tab portion.

23. A method of using TENS electrodes, comprising the steps of:
  (a) applying one electrode according to claim 20 extraorally to facial skin of a mammal, and
  (b) applying a second electrode according to claim 20 to facial skin of a mammal.

24. An electrode, comprising:
  a non-conductive flexible backing having an electrically conductive surface contacting both a field of conductive adhesive and two opposing fields of biocompatible pressure sensitive adhesive,
  wherein the flexible backing comprises a tab portion and a pad portion, and
  wherein the two opposing fields of biocompatible pressure sensitive adhesive contact opposing locations on the pad portion proximal and distal to the tab portion.

25. The electrode according to claim 24, wherein the field of conductive adhesive contacts only the pad portion.

\* \* \* \* \*